United States Patent
Daphna et al.

(10) Patent No.: US 11,079,613 B2
(45) Date of Patent: Aug. 3, 2021

(54) CONTACT LENS DRUG DEPOT

(71) Applicant: Eyeyon Medical Ltd., Nes Ziona (IL)

(72) Inventors: Ofer Daphna, Beit Elazari (IL); Brian Levy, Tampa, FL (US); Nahum Ferera, Petah Tikva (IL)

(73) Assignee: EyeYon Medical Ltd., Nes Ziona (IL)

( * ) Notice: Subject to any disclaimer, the term of this patent is extended or adjusted under 35 U.S.C. 154(b) by 241 days.

(21) Appl. No.: 15/947,826

(22) Filed: Apr. 8, 2018

(65) Prior Publication Data
US 2018/0224670 A1 Aug. 9, 2018

Related U.S. Application Data

(63) Continuation-in-part of application No. 15/422,599, filed on Feb. 2, 2017, now abandoned, and a continuation-in-part of application No. 14/814,521, filed on Jul. 31, 2015, now Pat. No. 9,927,632, and a continuation of application No. 13/785,157, filed on Mar. 5, 2013, now Pat. No. 9,097,915.

(51) Int. Cl.
*G02C 7/04* (2006.01)
*A61F 9/00* (2006.01)

(52) U.S. Cl.
CPC .............. *G02C 7/04* (2013.01); *A61F 9/0017* (2013.01); *G02C 7/047* (2013.01); *G02C 7/049* (2013.01); *G02C 2202/06* (2013.01)

(58) Field of Classification Search
CPC . G02C 7/04–049; G02C 2202/06; A61F 2/14; A61F 9/0017
USPC .............. 351/159.02, 159.04, 159.34
See application file for complete search history.

(56) References Cited

U.S. PATENT DOCUMENTS

| | | | | |
|---|---|---|---|---|
| 3,485,244 A | * | 12/1969 | Rosen Hyman | A61F 9/00 351/159.02 |
| 5,270,051 A | * | 12/1993 | Harris | A61F 9/0017 424/427 |
| 6,010,219 A | * | 1/2000 | Stoyan | G02C 7/047 351/159.23 |
| 8,864,306 B2 | * | 10/2014 | de Juan, Jr. | G02C 7/049 351/159.04 |
| 2006/0276777 A1 | * | 12/2006 | Coroneo | A61F 9/0008 606/5 |

(Continued)

FOREIGN PATENT DOCUMENTS

GB 2401954 A * 11/2004 .............. G02C 7/04

*Primary Examiner* — Travis S Fissel
(74) *Attorney, Agent, or Firm* — Dekel Patent Ltd.; David Klein

(57) ABSTRACT

A method includes placing a contact lens over a cornea of an eye. The contact lens includes a central convex disc, a peripheral curved portion that extends radially from the disc, an annular groove formed in the disc on the posterior portion, and one or more apertures formed in the groove. A drug substance is placed over the anterior portion of the contact lens. The groove is in contact with the cornea and is a depot for the drug substance. The groove is in fluid connection with the anterior portion of the lens via the one or more apertures. The drug substance moves in an undiluted manner to the groove and the contact lens holds the drug substance in contact with the cornea, unaffected by blinking or tear exchange, facilitating enhanced bioavailability to the cornea of the drug substance.

9 Claims, 2 Drawing Sheets

(56) References Cited

U.S. PATENT DOCUMENTS

| | | | |
|---|---|---|---|
| 2007/0122450 A1* | 5/2007 | Osio Sancho | G02C 7/047 424/428 |
| 2009/0171305 A1* | 7/2009 | El Hage | A61F 2/14 604/294 |
| 2009/0311251 A1* | 12/2009 | Auf Der Maur | A61K 39/39591 424/133.1 |
| 2010/0036488 A1* | 2/2010 | de Juan, Jr. | A61F 2/142 623/5.16 |

* cited by examiner

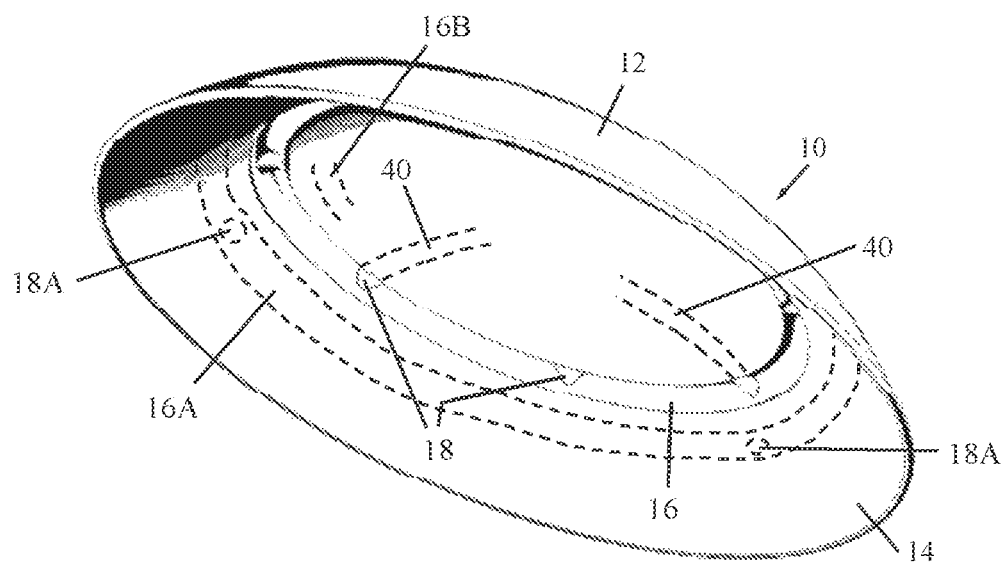
FIG. 1
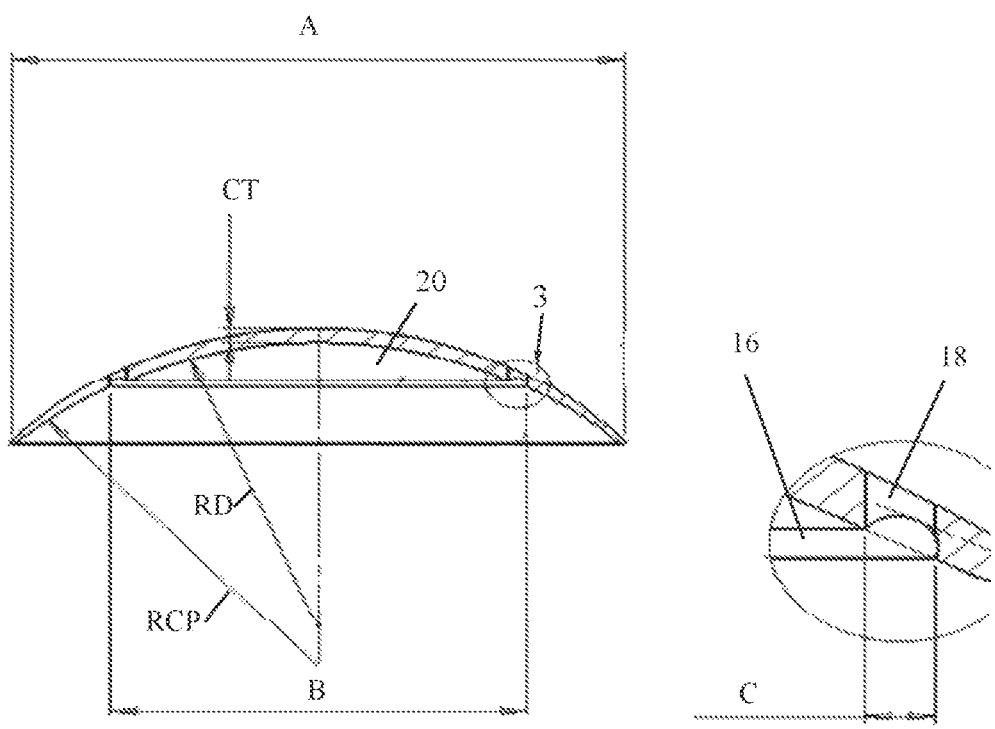
FIG. 2
FIG. 3

CONTACT LENS DRUG DEPOT

CROSS-REFERENCE TO RELATED APPLICATIONS

This application is a continuation-in-part of U.S. patent application Ser. No. 15/422,599, filed Feb. 2, 2017, which is a continuation-in-part of U.S. patent application Ser. No. 14/814,521, filed Jul. 31, 2015, which is a continuation of U.S. patent application Ser. No. 13/785,157, filed Mar. 5, 2013, now U.S. Pat. No. 9,097,915, which are all incorporated herein by reference.

FIELD OF THE INVENTION

The present invention relates generally to contact lenses and in particular to contact lenses designed to compensate for an over-hydrated, edematous cornea.

BACKGROUND OF THE INVENTION

U.S. Pat. No. 8,096,655 to Daphna describes a hyperosmotic contact lens designed to treat corneal edema. The hyper-osmotic contact lens absorbs fluid from an edematous cornea by the force of an osmotic gradient. The hyperosmotic contact lens is designed as a microcontainer with walls that are thin relative to its general dimensions, and is shaped as a lens with anterior and posterior walls, which define and bound a hyper-osmotic chamber. The posterior wall, which is the area in which the cornea and the contact lens overlap, is made of a selective water permeable membrane. In this area, water from the edematous cornea can flow out of the cornea into the hyper-osmotic chamber by the force of osmosis, thus dehydrating the cornea itself. The hyper-osmotic chamber may contain a hyper-osmotic transparent medium such as dry hydrogel or solution such as glycerol, salts, etc.

U.S. Pat. No. 8,440,217 describes a contact lens loaded with a drug and the carriers which carry the drug. The lens has a mechanical and optical structure formed by the core polymer included within the lens. The drug is released from the contact lens while the lens is adhered to the eye during a continuous period of time.

The drug is mixed with an aqueous liquid to form a mix that is conjugated to a polymer to create a polymer matrix in which the drug is covalently bonded to each repeating unit of the polymer. If the drug is water soluble, the drug is trapped within a network of tiny interconnected, water-filled channels in the polymer matrix. If the drug is not water soluble, the drug is trapped within spaces (e.g., nano-spaces) in the polymer matrix, and slowly migrates or diffuses into the channels of the polymer matrix. The channels open up and release the drug as the channels come into contact with fluid (i.e., aqueous humor) on the eyeball of the eye. By varying the water content of the formed mix of the drug and the aqueous liquid, the size of the channels may be varied to control the rate at which the drug leaks out of the lens and onto the eye. The nanostructure of the drug-infused contact lens, with the inter-connected channels, allows gases, salts, and nutrients to readily diffuse across the lens.

One of the disadvantages of U.S. Pat. No. 8,440,217 is that the drug must be compatible with the lens material, which limits the type of drugs which can be administered. Another problem is that the drug, once released from the lens material, may be rapidly washed away by blinking or tears. There is no structure in the lens which ensures the drug is contact with the cornea for a prolonged period of time.

SUMMARY OF THE INVENTION

The present invention relates to a contact lens, which provides structure different than U.S. Pat. No. 8,096,655, as is described further in detail hereinbelow.

The contact lens of the invention is used as a drug depot to enable the drug, regardless of the drug or contact lens chemistry, to remain in contact with the cornea as long as possible to enhance the bioavailability of the undiluted drug. In the prior art, once a topical drug is placed on the naked corneal surface the residence time of the active drug is literally a matter of minutes. This is due to the rapid movement and depletion of the drug on the corneal surface by blinking of the eye and the dilution of the drug by the tears resulting in the majority of the drug being flushed into the inferior and superior nasolacrimal ducts and into the systemic circulation. In order to enhance the bioavailability the drug needs to remain relatively static, unaffected by the blink and at full concentration for as long as possible. To enable this to occur, the contact lens of the present invention serves as a drug depot by means of the unique structure of the lens using a channel or groove on the inner portion of the lens which is in contact with the corneal surface and act as a "lake" or depot for the drug. This channel is connected to the anterior portion of the lens, which is in contact with the external environment through a fenestration (a small aperture which acts as another channel) allowing for fluids placed on the surface of the lens to move in a relatively undiluted manner to the posterior surface channel which is in contact with the anterior corneal surface. The lens then holds the drug in contact with the cornea, relatively unaffected by blinking or tear exchange, facilitating enhanced bioavailability to the cornea and allowing for a greater concentration of the drug to be in contact with the corneal surface for longer periods of time than a topical drop.

There is provided in accordance with an embodiment of the present invention a method including placing a contact lens over a cornea of an eye, the contact lens having a posterior portion in contact with the cornea and an anterior portion facing an external environment which is external to the eye, and wherein the contact lens includes a central convex disc, a peripheral curved portion that extends radially from the disc, an annular groove formed in the disc on the posterior portion, and one or more apertures formed in the groove, and placing a drug substance over the anterior portion of the contact lens, wherein the groove on the posterior portion is in contact with the cornea is a depot for the drug substance, the groove being in fluid connection with the anterior portion via the one or more apertures, such that the drug substance moves in an undiluted manner to the groove which is in contact with the cornea and the contact lens holds the drug substance in contact with the cornea, unaffected by blinking or tear exchange, facilitating enhanced bioavailability to the cornea of the drug substance.

BRIEF DESCRIPTION OF THE DRAWINGS

The present invention will be understood and appreciated more fully from the following detailed description taken in conjunction with the drawings in which:

FIG. 1 is a simplified front view illustration of a contact lens, constructed and operative in accordance with an embodiment of the present invention.

FIG. 2 is a cross sectional view of the contact lens.

FIG. 3 is an enlarged cross-section of a hole and annular groove of the lens.

DETAILED DESCRIPTION OF EMBODIMENTS

Figure 4:
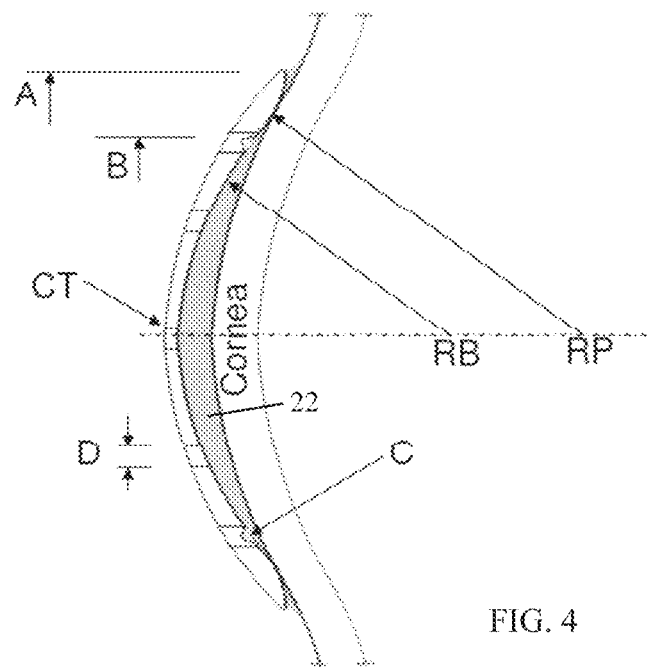
FIG. 4 is a simplified side view of the contact lens mounted on an eye, in accordance with an embodiment of the present invention.

Reference is now made to FIG. 1, which illustrates a contact lens 10, constructed and operative in accordance with an embodiment of the present invention.

Contact lens 10 includes a central convex disc 12 from which radially extends a peripheral curved portion 14. Central convex disc 12 and peripheral curved portion 14 can have the same curvature or different curvatures. An annular groove 16 is formed at the interior (i.e., posterior side) junction of disc 12 and peripheral curved portion 14. In an alternative embodiment, annular groove 16 may be radially inwards of this junction. In another alternative embodiment, annular groove 16 may be radially outwards of this junction. One or more apertures (through holes) 18 may be formed in groove 16. In an alternative embodiment, the one or more apertures 18 may be radially inwards of annular groove 16. In another alternative embodiment, the one or more apertures 18 may be radially outwards of annular groove 16. In one embodiment, there are 6 apertures 18; in another embodiment there are 8 apertures 18, but the invention is not limited to these numbers.

Central convex disc 12 is made of a material that is oxygen permeable and dimensionally stable for use as a contact lens. A preferred example is G4X p-GMA/HEMA (hioxifilcon D), with water content in the range of approximately 50-75%, commercially available from Benz Research & Development, Sarasota, Fla., US. The invention is not limited to this material and other suitable soft or hard materials may be used (e.g., GP PMMA—gas permeable polymethylmethacrylate). For example, the lens may be made of CONTAFLEX GM, commercially available from Contamac Ltd., UK, which is a highly water retentive terpolymer based on glycerol methacrylate.

In one embodiment, the inner volume of lens 10, preferably that of central convex disc 12, defines a reservoir 20 (which may be a hyper-osmotic chamber, but in some embodiments is not hyper-osmotic) (seen in FIG. 2) for supporting therein a substance 22 (FIG. 4), which may be a hyper-osmotic transparent medium such as, but not limited to, dry hydrogel, etc., or solution such as, but not limited to, glycerol, salt solution, etc., or non-hyper-osmotic substances, and which may include antibiotics, steroids and other medicinal substances. Substance 22 may also have suitable refraction and transparency properties, which may be selected for modifying vision of a patient.

If substance 22 is hyper-osmotic, substance 22 creates a molecular concentration gradient and thus osmotic pressure gradient between the cornea and hyper-osmotic chamber 20. The osmotic pressure gradient results in a net flow of fluid from the cornea directly into hyper-osmotic chamber 20 by osmosis, thus dehydrating the cornea. Lens 10 can be constructed to reach a steady state net fluid flow or not to reach steady state.

Lens 10 has a suitable volume to enable functioning for a sufficient duration until it is full. Accordingly, contact lens 10 may be used for daily treatment, partial daily treatment or overnight treatment, or any other treatment period which is needed for the patient treatment when it is mounted upon a cornea in an edematous state. Contact lens 10 may be sized to fit over the cornea to the limbus, or alternatively may extend over the limbus.

In another embodiment, chamber 20 is not filled with any substance 22, but instead simply fits over the cornea or cornea and limbus or beyond the limbus. It has been found that the chamber 20 defined by central convex disc 12, even when initially empty (that is, devoid of a hyper-osmotic substance, but, for example, containing air), can create an osmotic pressure gradient that results in a net flow of fluid from the cornea directly into hyper-osmotic chamber 20 by osmosis, thus dehydrating the cornea. A tear film is created, due to the osmotic pressure gradient, between the lens 10 and the cornea. Due to the groove 16 and apertures 18, the tear film creates a surface tension underneath the lens 10 which is relatively trapped and slow to escape. (The apertures 18 are small so the drops do not flow past them but instead are trapped due to surface tension). The entrapped salty tear film increases the hyper-osmotic pressure, which synergistically increases dehydration of the cornea. The structure of the apertures and lens is such that any liquid drop that placed on the exterior surface of the lens will be drawn through the relatively unidirectional apertures 18 to the interior of the lens. Thus, the lens serves as a trap for fluids, such as a hypertonic solution or any other drug.

Optionally, the lens 10 can be heavier at its bottom portion, which may increase the stability of the lens against any torsional movement and maintain the lens in place.

Reference is now made to FIGS. 2 and 4. Non-limiting, exemplary values of lens dimensions are now described.

In one embodiment of the invention, the parameters are as follows:

A overall lens diameter (including peripheral curved portion 14)=11.50 mm

D diameter of aperture 18=0.5 mm

B reservoir diameter (diameter of hyper-osmotic chamber 20)=7.50 mm

C thickness of annular groove 16=0.40 mm

CT center thickness=0.4 mm (see FIG. 3)

RP peripheral eye radius

RB reservoir radius is 0.3 mm steeper than central eye flat meridian

RD radius (curvature) of central convex disc 12=8.60 mm

RCP radius (curvature) of peripheral curved portion 14=8.60 mm

In another embodiment of the invention, the parameters are as follows:

A overall lens diameter (including peripheral curved portion 14)=15.00 mm

D diameter of aperture 18=1.50 mm

B reservoir diameter (diameter of hyper-osmotic chamber 20)=9.50 mm

C thickness of annular groove 16=0.40 mm

CT center thickness=0.25 mm

RP peripheral eye radius

RB reservoir radius is 0.3 mm steeper than central eye flat meridian

RD radius (curvature) of central convex disc 12=7.80 mm

RCP radius (curvature) of peripheral curved portion 14=9.60 mm

In still another embodiment of the invention, the parameters are as follows:

A overall lens diameter (including peripheral curved portion 14)=14.00 mm

D diameter of aperture 18=0.5 mm

B reservoir diameter (diameter of hyper-osmotic chamber 20)=9.50 mm

C thickness of annular groove 16=0.40 mm

CT center thickness=0.4 mm

RP peripheral eye radius

RB reservoir radius is 0.3 mm steeper than central eye flat meridian

RD radius (curvature) of central convex disc 12=8.60 mm

RCP radius (curvature) of peripheral curved portion 14=8.60 mm

In yet another embodiment of the invention, the parameters are as follows:

A overall lens diameter (including peripheral curved portion 14)=11.00 mm

D diameter of aperture 18=0.5 mm

B reservoir diameter (diameter of hyper-osmotic chamber 20)=7.50 mm

C thickness of annular groove 16=0.30 mm

CT center thickness=0.4 mm

RP peripheral eye radius

RB reservoir radius is 0.3 mm steeper than central eye flat meridian

RD radius (curvature) of central convex disc 12=8.60 mm

RCP radius (curvature) of peripheral curved portion 14=8.80 mm

It is noted that in the first and fourth examples, the lens basically covers just the cornea, whereas in the second and third embodiments the lens extends to the limbus and beyond.

As shown in broken lines in FIG. 1, as another option one or more arcuate grooves 40 may be formed at least partially in the spherical longitudinal direction across the inner surface of central convex disc 12. Grooves 40 may extend from apertures 18.

Figure 5:
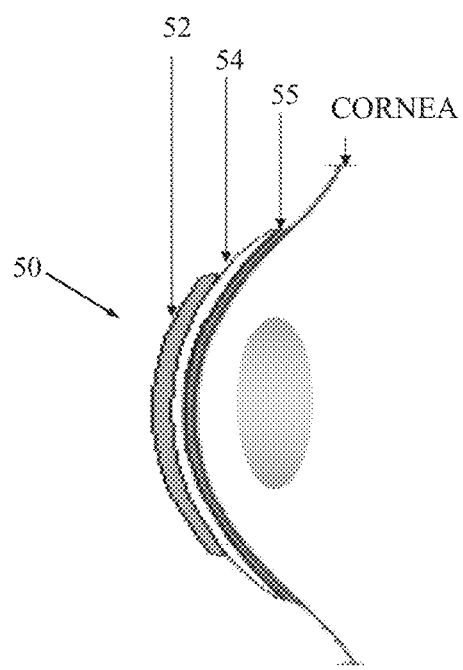
FIG. 5 is a simplified side view of a contact lens mounted on an eye, in accordance with another embodiment of the present invention.

Reference is now made to FIG. 5, which illustrates a contact lens 50, constructed and operative in accordance with another embodiment of the present invention.

Contact lens 50 includes an anterior lens 52 that is mounted over a posterior lens 54, which in turn is mounted on the cornea C of the eye. A tear film 55 may be present between posterior lens 54 and the cornea. Without limitation, anterior lens 52 and posterior lens 54 may be made of G4X p-GMA/HEMA (hioxifilcon D), respectively with 73% and 54% water content; they may be made alternatively of CONTAFLEX GM. Dimensions of anterior lens 52 may be similar to the first above example, whereas posterior lens 54 may be similar to the second above example. The invention is not limited to these values.

The hyper-osmotic contact lens described above is a contact lens that creates a cavity above the center of the cornea. Without limitation, the cavity volume is estimated at ~10 μl and is generally at a height between 0-200 μm above the corneal surface. This cavity can store substances, such as but not limited to, hypertonic drops, for a long duration and by doing so extracts fluids by osmosis from the cornea.

In one application, the contact lens of the invention is used as a drug depot to enable the drug, regardless of its chemistry, to remain in contact with the cornea as long as possible to enhance the bioavailability of the drug. In order to enhance the bioavailability the drug needs to remain relatively static, unaffected by the blink and at full concentration for as long as possible. The contact lens 10 serves as a drug depot by means of the groove 16 or 40 on the inner portion of the lens which is in contact with the corneal surface and act as a "lake" or depot for the drug. The groove 16 or 40 is connected to the anterior portion of contact lens 10, which is in contact with the external environment through fenestration 18 (aperture 18) which acts as another channel allowing for fluids placed on the anterior surface of the lens 10 to move in a relatively undiluted manner to the posterior surface groove 16 or 40 which is in contact with the anterior corneal surface. Contact lens 10 holds the drug in contact with the cornea, relatively unaffected by the blink or tear exchange, facilitating enhanced bioavailability to the cornea and allowing for greater concentrations of the drug to be in contact with the corneal surface for longer periods of time.

The contact lens can be used in a variety of applications. The lens provides increased contact time of the medication (any drug substance) with the eye in order to maximize the treatment effect. For example, the lens may be used to treat corneal infections, uveitis, dry eye, allergic conjunctivitis and any other condition requiring the medication to be in contact for a longer period of time than a topical drop. The contact lens can also be used in a corneal collagen cross-linking procedure, for intra-operative use to enhance the procedure by holding riboflavin in place on the corneal surface rather than the current technique requiring continuous application of drops to the cornea for approximately 20 minutes.

What is claimed is:

1. A method comprising:

placing a contact lens over a cornea of an eye, said contact lens having a posterior portion in contact with the cornea and an anterior portion facing an external environment which is external to the eye, and wherein said contact lens comprises a central convex disc, a peripheral curved portion that extends radially from said disc, an annular groove formed in said disc on said posterior portion, and one or more apertures formed in said groove; and placing a drug substance over the anterior portion of said contact lens, wherein said groove on said posterior portion that is in contact with the cornea is a depot for the drug substance, said groove being in fluid connection with said anterior portion via said one or more apertures, such that the drug substance moves to said groove which is in contact with the cornea and said contact lens holds the drug substance in contact with the cornea, without detrimental effects from blinking or tear exchange, facilitating enhanced bioavailability to the cornea of the drug substance.

2. The method according to claim 1, wherein said drug substance comprises a hypertonic solution.

3. The method according to claim 1, further comprising using said lens to provide increased contact time of said drug substance with the eye.

4. The method according to claim 1, further comprising using said lens to treat recurrent corneal erosion syndrome (RCE).

5. The method according to claim 1, further comprising using said lens to treat dry eye syndrome.

6. The method according to claim 1, further comprising using said lens to treat uveitis.

7. The method according to claim 1, further comprising using said lens to treat an allergy.

8. The method according to claim 1, further comprising using said lens in a corneal collagen cross-linking procedure, for intra-operative use or reducing procedure time.

9. The method according to claim 1, wherein an inner surface of said groove contacts the cornea.

* * * * *